United States Patent
McReynolds et al.

(10) Patent No.: US 8,173,139 B1
(45) Date of Patent: May 8, 2012

(54) HIGH ENERGY ELECTRON BEAM IRRADIATION FOR THE PRODUCTION OF IMMUNOMODULATORS IN POULTRY

(75) Inventors: Jackson L. McReynolds, Bryan, TX (US); Suresh Pillai, College Station, TX (US); Palmy Rose Rajan Jesudhasan, College Station, TX (US); Martha Lucia Cepeda Hernandez, Waltham, MA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 182 days.

(21) Appl. No.: 12/556,907

(22) Filed: Sep. 10, 2009

Related U.S. Application Data

(60) Provisional application No. 61/101,239, filed on Sep. 30, 2008.

(51) Int. Cl.
*A61K 39/112* (2006.01)
*A61K 39/02* (2006.01)
*A61K 49/00* (2006.01)

(52) U.S. Cl. .... 424/258.1; 424/9.1; 424/9.2; 424/184.1; 424/234.1; 424/278.1; 424/823; 424/824; 424/825; 424/826; 372/1; 372/9; 372/81; 372/87

(58) Field of Classification Search .................. 424/9.1, 424/9.2, 184.1, 234.1, 258.1, 278.1, 823, 424/824, 825, 826; 372/1, 9, 81, 87
See application file for complete search history.

*Primary Examiner* — Rodney P. Swartz
(74) *Attorney, Agent, or Firm* — John Eado; Randall E. Deck; Lesley Shaw

(57) ABSTRACT

Populations of *Salmonella* in animals may be substantially reduced by treatment with a vaccine composition which has been produced by exposing whole, intact cells of a *Salmonella* species to irradiation with an electron beam under conditions effective to kill the cells. The electron beam irradiated cells of *Salmonella* are effective for stimulating protective immune responses in the animals against the *Salmonella*. Induction of these immune responses significantly reduces or eliminates the colonization of the animal by the *Salmonella*, and consequently reduces or eliminates the shedding of *Salmonella* in the feces of the animals.

11 Claims, 6 Drawing Sheets

| Treatment1 | SE Culture Positive Hens | | | |
|---|---|---|---|---|
| | Liver | Spleen | Ceca | Ovaries |
| Negative Control | 0/29 | 0/29 | 0/29 | 0/29 |
| Positive Control | 21/29 | 21/29 | 27/29 | 11/29 |
| E-B Killed SE | 4/30 | 3/30 | 7/30 | 1/30 |

FIGURE 2

HIGH ENERGY ELECTRON BEAM IRRADIATION FOR THE PRODUCTION OF IMMUNOMODULATORS IN POULTRY

CROSS-REFERENCE TO RELATED APPLICATIONS

This application claims the benefit under 35 U.S.C. 1.19(e) of U.S. provisional 61/101,239, filed Sep. 30, 2008, the contents of which are incorporated by reference herein.

BACKGROUND OF THE INVENTION

1. Field of the Invention

This invention relates to a novel vaccine against *Salmonella* which offers superior protection and safety over existing vaccines.

2. Description of the Prior Art

Despite the efforts of researchers and public health agencies, the incidence of human infections from enteropathogenic bacteria such as *Salmonella, E. coli* 0157:H7, and *Campylobacter* has increased over the past 20 years. For example, the number of actual reported cases of human *Salmonella* infection exceeds 40,000 per year. However, the Communicable Disease Center estimates that the true incidence of human *Salmonella* infections in the U.S. each year may be as high as 2 to 4 million. The USDA Economic Research Service has recently reported that the annual cost of the food borne illnesses caused by six common bacterial pathogens, *Campylobacter* spp., *Clostridium perfringens, Escherichia coli* 0157:H7, *Listeria monocytogenes, Salmonella* spp., and *Staphylococcus aureus*, ranges from 2.9 billion to 6.7 billion dollars (Food Institute Report, USDA, AER, December, 1996). In addition to the impact of enteric pathogens on human health, many of these bacteria also cause significant infections in animals. For example, Salmonella infections in swine alone cost the United States swine industry more than 100 million dollars annually (Schwartz, 1990, "Salmonellosis in Midwestern Swine", In: Proceedings of the United States Animal Health Assoc., pp. 443-449).

Animal food products remain a significant source of human infection by these pathogens. Contamination of meat and poultry with many bacterial food-borne pathogens, including the particularly onerous pathogens *Campylobacter* spp., *Escherichia coli* 0157:H7, and *Salmonella* spp., often occurs as a result of exposure of the animal carcass to ingesta and/or fecal material during or after slaughter. Any of the above-mentioned pathogens can then be transmitted to humans by consumption of meat and poultry contaminated in this manner.

Preharvest control of enteropathogenic bacteria is a high priority to the food industry. However, few products have been developed to facilitate such efforts. Currently, preharvest pathogen control within the poultry industry may be accomplished through use of competitive exclusion cultures or probiotics. Moreover, the administration of competitive exclusion cultures is preferably targeted to very young animals. Immune lymphokines (ILK) have also been developed for protecting poultry from colonization with enteric pathogens as described by Ziprin et al. (1989, Poult. Sci., 68:1637-1642), McGruder et al. (1993, Poult. Sci., 72:2264-2271), Ziprin et al. (1996, Avian Dis., 40:186-192), and Tellez et al. (1993, Avian Dis., 37:1062-1070), and more recently by Kogut et al. (U.S. Pat. Nos. 5,891,443 and 5,691,200). Most recently, Anderson et al. (U.S. Pat. No. 6,475,527) disclosed that chlorates substantially reduce populations of enteropathogenic bacteria in the alimentary tract when administered orally, or alternatively, reduce the populations of these enteropathogens present as contaminants on the surface of the animals following external application of chlorates. However, despite these and other advances, the need persists for technologies for controlling enteric pathogens in animals, and particularly for the treatment of animals immediately prior to slaughter.

SUMMARY OF THE INVENTION

We have now discovered a method and compositions for controlling or inhibiting *Salmonella* colonization in animals. Populations of *Salmonella* may be substantially reduced by treatment of the animals with a vaccine composition which has been produced by exposing whole, intact cells of a *Salmonella* species to a shower of electron particles by irradiation with an electron beam at doses effective to kill the cells. These electron beam irradiated cells of *Salmonella* are effective for stimulating protective immune responses in the animals against the *Salmonella*. Induction of these immune responses significantly reduces or eliminates the colonization of the animal by the *Salmonella*, and consequently reduces or eliminates the shedding of *Salmonella* in the feces of the animals.

In accordance with this discovery, it is an object of this invention to provide a method for controlling food borne *Salmonella* in animals.

Another object of this invention is to provide a method for controlling *Salmonella* bacteria in the gastrointestinal tract of animals.

Yet another object of this invention is to provide a method for significantly reducing the populations of *Salmonella* in meat producing animals prior to slaughter.

Other objects and advantages of this invention will become readily apparent from the ensuing description.

BRIEF DESCRIPTION OF THE DRAWINGS

FIG. 2 shows the results from Example 1 of the colonization by *Salmonella enteritidis* in the organs of laying hens.

DETAILED DESCRIPTION OF THE INVENTION

Figure 1:
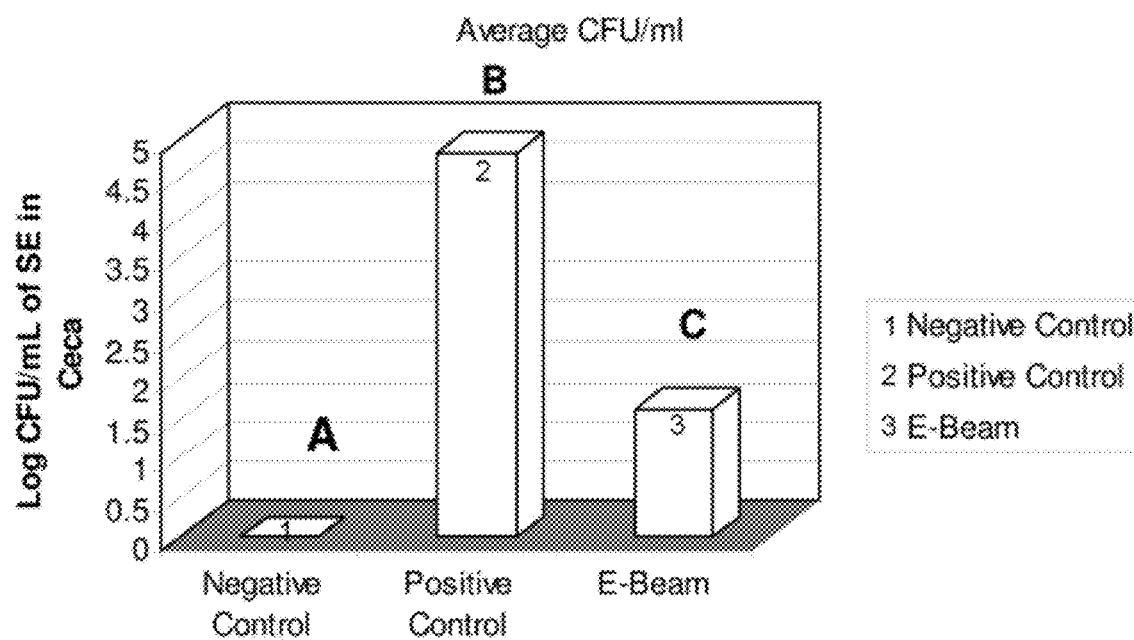
FIG. 1 shows the results from Example 1 of the colonization by *Salmonella enteritidis* in the ceca of laying hens.

As used herein, "vaccine" is defined herein in its broad sense to refer to any type of biological agent in an administratable form capable of stimulating an immune response in an animal inoculated with the vaccine. For the purposes of this invention, the vaccine comprises the electron beam irradiated cells of *Salmonella*.

The irradiation process of this invention may be used to prepare vaccines to any species of *Salmonella*. However, the invention is particularly used for the preparation of vaccines to *S. typhimurium* and *S. enteritidis*, which are frequently implicated in cases of food-borne illness.

The vaccine of this invention is a killed cell preparation or bacterin. Propagation of the bacterium for preparation of the vaccine may be effected by culture under any conventional conditions and on media which promote its growth. Although a variety of conventional solid and liquid media may be suitable for use herein, growth in liquid culture is particularly preferred for large scale production. Without being limited thereto, conventional tryptic soy broth is preferred. Optimal growth is effected under aerobic conditions at approximately 37° C. with agitation for about 18 to 24 hours.

Following their propagation and recovery, to produce the vaccine, viable cells of *Salmonella* are exposed to a high energy electron beam at a sufficient dose for a sufficient period of time to kill (i.e., inactivate) the cells. We have unexpectedly found that cells of *Salmonella* may be killed by irradiation with a high energy electron beam light while still retaining their antigenicity. This irradiation does not substantially alter the specificity of the cell surface antigens on the killed cells relative to the untreated cells such that the killed cells retain their ability to elicit a protective immune response. Although the electron beam irradiation severely damages the cell's DNA, cell surface antigens and properties are not substantially affected.

A variety of conventional high energy linear accelerators are suitable for generating the E-Beam use herein, although linear accelerators having beam energies above approximately 1.0 MeV are preferred. Without being limited thereto, it is envisioned that other suitable electron beam accelerators include electrostatic direct-current (DC), electrodynamic DC, linear accelerators (LINACS), magnetic-induction LINACs, and continuous-wave (CW) accelerators. For practical purposes, the cells are preferably prepared by suspension in a liquid, for example, the culture medium or a diluent such as physiologically buffered saline, for irradiation. In a preferred embodiment, the suspension is prepared/adjusted to provide an approximate concentration between $1\times10^6$ and $1\times10^7$ CFU/ml.

An effective electron beam treatment for killing the cells is defined herein as that which kills 99.99999% or more of the viable cells, without destroying the cell surface properties or lysing the cells but still retaining the ability of the cells to elicit an antibody response in the animal. While treatments killing 100% of all viable cells would typically be preferred, the skilled practitioner will recognize 100% cell death may not always be readily obtainable. The electron beam dose to effect this killing may vary somewhat, but should not be so great as to disrupt (lyse) the cells or significantly alter or destroy cell-surface antigens, and may be readily determined by routine testing. However, as a practical matter and without being limited thereto, the cells should preferably receive an electron beam radiation dosage between about 2 to about 5 kilograys (kGy, where 1 kGy is equal to 1,000 Joules per kilogram), most preferably between about 2.5 to about 4.0 kGy. The radiation dose necessary to achieve efficient kill will of course vary with the optical density of the *Salmonella* culture or suspension, the genetics of the particular *Salmonella* species or strain, the physical state of the culture (lyophilized, in suspension, or frozen), the material composition of the sample container and packaging, the electron beam current (measured in milliamperes), and the path length of the medium containing the cells (i.e., the depth through which the radiation must pass) and should be selected to provide the desired radiation dose. The temperature of the treatment also is not critical, although very high temperatures inducing protein denaturization should be obviously avoided. The process temperature should be between about 1 to 10° C. to avoid thermal inactivation of the organisms.

Killed cells of *Salmonella* are prepared for administration by formulation in an immunologically effective amount or dosage to the animal. The dose may further include pharmaceutically acceptable carriers and adjuvants known in the art. An immunologically effective amount or dosage is defined herein as being that amount which will induce complete or partial immunity (elicit a protective immune response) in a treated animal and consequently reduce or eliminate the population of *Salmonella* therein and/or reduce the incidence of infection by the *Salmonella* against subsequent challenge with the same species of *Salmonella*. Immunity is preferably considered as having been induced in a population of treated animals when the level of protection for the population, evidenced by one or more of: reducing *Salmonella* shedding, reducing the average *Salmonella* concentration in the different target organs, reducing the duration of *Salmonella* colonization, or lowering the percentage of animals colonized with *Salmonella*, is significantly higher than that of an unvaccinated control group (measured at a confidence level of at least 80%, preferably measured at a confidence level of 95%). Suitable amounts may be readily determined by the practitioner skilled in the art by routine testing, and will vary with the route of administration, and the age and size of the animal. In the preferred embodiment, when treating fowl by intramuscular, subcutaneous or IV injection, the dose will contain approximately $1\times10^5$ to $1\times10^8$ cells of the bacterium, most preferably about $1\times10^6$ cells (generally administering about 1 ml of cell suspension). Although greater amounts of cells may be administered, use of such higher levels is generally considered impractical. The dose is preferably the same for administration by in ovo injection. For oral administration, it is envisioned that effective doses should be increased, preferably to approximately 5 ml or more.

As noted above, the killed cells may be formulated in a pharmaceutically acceptable carrier such as water, physiological saline, mineral oil, vegetable oils, aqueous sodium carboxymethyl cellulose, or aqueous polyvinylpyrrolidone. The vaccine formulations may also contain optional adjuvants, antibacterial agents or other pharmaceutically active agents as are conventional in the art. Without being limited thereto, suitable adjuvants include but are not limited to mineral oil, vegetable oils, alum, and Freund's incomplete or complete adjuvant. Still other preferred adjuvants and carriers can include micro and nanoparticles or beads of biocompatible matrix materials, or lyophilized pellets. The nano and microparticles may be composed of any biocompatible matrix materials as are conventional in the art, including but not limited to, agar and polyacrylate. The practitioner skilled in the art will recognize that other carriers or adjuvants may be used as well. For example, other adjuvants which may be used are described by Webb and Winkelstein [in Basic & Clinical Immunology, Stites et al. (ed.), fifth edition, Lange Medical Publications, Los Altos, Calif., 1984, pages 282-285], the contents of which are incorporated by reference herein. For oral administration, the vaccine may be formulated with the animal's drinking water or feed. Agents conventional in the art for the treatment of the animals, including those for the treatment of pathogens, may also be formulated with the vaccine. Suitable agents include but are not limited to other vaccines, antitoxins, deworming agents, or therapeutic antibiotics. Non-therapeutic levels of antibiotics may also be administered to the animals as is conventional in the art. In a particularly preferred embodiment for the treatment of poultry, the killed cell vaccine is administered with synthetic oligonucleotides containing CpG dinucleotide (CpG ODN) which mimic microbial DNA and stimulate both innate and adaptive immunity against Gram-positive *Enterococcus gallinarum*.

In accordance with an optional embodiment, the killed cells may be incorporated into micro and linked to nanoparticles or microcapsules to prolong the exposure of the antigenic material to the subject animal and hence increase the duration of protective immunity. The micro and nanoparticles and capsules may be formed from a variety of well-known inert, biocompatible matrix materials using techniques conventional in the art. Without being limited thereto, suitable matrix materials include natural or synthetic polymers such as alginates, poly(lactic acid), poly(lactic/glycolic acid), poly (caprolactone), polycarbonates, polyamides, polyanhydrides, polyortho esters, polyacetals, polycyanoacrylates, polyurethanes, ethylene-vinyl acetate copolymers, polystyrenes, polyvinyl chloride, polyvinyl fluoride, poly(vinyl imidazole), chlorosulphonated polyolefins, polyethylene oxide, and particularly agar and polyacrylates. Examples of techniques for incorporation of cells or other material into microparticles or encapsulation which may be used herein are described by Sparks [Microencapsulation, In: Kirk-Othmer Encyclopedia of Chemical Technology, third edition, John Wiley & Sons, New York, (1981), volume 15, pages 470-493], Kydonius [controlled Release Technologies: Methods, Theories, and Applications, CRC Press, Cleveland, Ohio, 1980], Gombotz et al. [U.S. Pat. No. 5,019,400], or Beck [U.S. Pat. No. 4,919,929], the contents of each of which are incorporated by reference herein.

The vaccine may be used for the treatment of a wide variety of animals, including primates, equine, and meat producing animals such as fowl, ovine, bovine, and porcine. However, without being limited thereto, the vaccine is preferably used for the treatment of meat-producing animals, particularly cattle, hogs, and most particularly poultry, including chickens, turkeys, ducks, and quail. The vaccine can be effectively administered anytime after the subject animal attains immunocompetence, and in the case of fowl, may also be administered in ovo. For practical purposes when administered in ovo, the vaccine is preferably injected on day 18 of incubation as is conventional in commercial hatchery operations.

The vaccines of the invention may be administered to the subject animal by any convenient route which enables the cells to elicit an immune response, such as by intramuscular, subcutaneous or IV injection, or by oral administration. However, injection is typically preferred. The vaccine may be administered in a single dose or in a plurality of doses. Dependent upon rearing conditions, the vaccine may be administered in multiple doses, the timing of which may be readily determined by the skilled artisan.

The following examples are intended only to further illustrate the invention and are not intended to limit the scope of the invention which is defined by the claims.

Example 1

A first trial was conducted to assess the effects therapeutic administration (IM) of the electron beam killed cell vaccine in reducing *Salmonella enteritidis* in laying hens.
Procedures
Preparation of *Salmonella enteritidis* Cells:
*Salmonella enteritidis* (SE) was obtained from USDA/ARS/SPARC/FFSRU. The SE strain was grown in TSB at 37° C. for 18-24 hours. The cells were then maintained and stored on TSA media and grown in 10 mL of TSB for 18-24 hours in a shaker water bath at 37° C. for growth.
Preparation of Irradiated Cells:
To make the overnight culture, one CFU was taken from the storage plate, put in 10 mL of TSB, and the culture was grown in 37° C. for 18-24 hours. Cells were washed and then resuspended in PBS. The optical density (OD) of the culture was measured and recorded, and adjusted to an OD of 0.5 by serial dilutions. This gave an approximate concentration of $1\times10^6$ CFU/mL. This suspension was transported to the High Energy Electron-beam (E-beam) Irradiation facility at Texas A&M University.

The concentration of ($1\times10^6$ CFU/ml of SE cells in log growth) was irradiated at 4.0 kGy to inactivate/kill the cells. These cells were kept refrigerated until administered via injection. The concentration of killed SE in the suspension was $1\times10^6$ CFU/ml.

The E beam treated suspension was plated out on TSA via serial dilutions to ensure no growth, and an OD reading was taken to ensure cell concentration with an optical OD of 0.5.
Feeding, Watering and Housing:
The single comb White Leghorn birds were kept in layer cages, one bird per cage and exposed to 16 hours of light and 8 hours of dark. They were fed a commercial layer feed formula from day of place to beginning of molt (Day 11). At this point the birds were taken off of all feed and allowed access solely to water ad libitum from cup drinkers supplied by a designated layer cage for that treatment.
Bird Vaccination
The birds were divided into 4 groups (birds that were bled were on the top row of the correlating cage).

|  | Pos/cage # | Neg/cage # | Cu/cage # | EB/cage # |
| --- | --- | --- | --- | --- |
| Rep 1 | 12 (6 bled)/6 | 12 (6 bled)/13 | 12 (6 bled)/12 | 12 (6 bled)/11 |
| Rep 2 | 12/2 | 12/14 | 12/9 | 12/10 |
| Rep 3 | 12/8 | 12/15 | 5/1 | 12/3 |
| Expected # positive of 36 | 22-27 | 2-4 | 5-6 | 5-6 |

Vaccination Emulsion
One to one ratio of solutions for the saline or E beam vaccine were mixed with Freund's adjuvant to aid the deliverance of the cells used for the vaccination. The solutions were mixed via glass syringes immediately before administration to ensure the emulsion stayed homogeneously mixed in solution for better vaccination delivery.
IM Vaccination Administration
The birds were vaccinated with the irradiated E beam cells at a concentration of $1\times10^6$ cfu/mL/bird in 2 different areas in the breast muscle on Day 0. Positive and negative controls were vaccinated with 1 mL saline. Six birds from each treatment were bled to achieve a blood titer level (SE) baseline for day 0. Negative birds were not vaccinated at all.
Bleeding
Six birds from each treatment were bled via the jugular vein at days 0, 14 and 23, day of vaccination, challenged and terminated, respectively. Blood once obtained was put into vacuum sealed tubes with an anticoagulant until tested with ELISA for the presence of antibodies.
Molting:
Day 4, post vaccination, the lights were adjusted to 8 L: 16 D and the birds were weighed and recorded. On day 11 the birds were taken off of feed completely but still had access to water ad libitum throughout the study. Post feeding the birds were withdrawn and weighed and recorded prior to sacrifice.
Challenge
On Day 14, the birds in all groups but the negative control were challenged with a fresh overnight SE culture with a concentration of $1\times10^6$ CFU/mL/bird (15 days post vaccination) via gavage. This determined the level of protection from the vaccine with an induced molt. Birds were bled to observe antibody titers via ELISA testing.

Necropsy

On Day 23, post vaccination, the birds were sacrificed via cervical dislocation. The spleen, liver, ceca, and ovaries were aseptically taken from each bird. The liver, spleen and ceca were cut in several plades to increase the surface area of the organ, and Rappaport-vassiliadis broth (RV) was added to the sample for SE enrichment and incubated at 37° C. and plated the following day for (+/−) scoring. Samples from the ceca were also direct plated, in which samples were serially diluted and plated on XLT4 media and incubated at 37° C. overnight. Plates were counted and recorded for positive CFU's.

Bacteriology Counts

To measure antibody titers, a *Salmonella enteritidis* agglutination kit was used as a diagnostic tool. Kit directions were followed as per labeled instructions.

ELISA

Antibody titrations of laying hens challenged with SE were conducted by ELISA as follows:

Antigen Coating
1. Prepare an antigen (100 μg/well) solution at the appropriate concentration ($10^{5-6}$) in carbonate-bicarbonate buffer (pH9.6) or PBS.
2. Pipette 200 μl of the above solution to each well of the microtiter plate.
3. Incubate at 37° C. for 30 min., or incubate (covered) overnight at 4° C.
4. Remove the coating solution.
5. Wash three times with PBS-T (10 mM phosphate buffer pH 7.4, 150 mM NaCl, 0.05% Tween 20).
6. Blocking step—5% BSA-PBS (10 mM phosphate buffer pH 7.4, 150 mM NaCl, 0.05% Tween 20+5% BSA or 3% skim milk) for 1 hour to prevent non-specific binding.
7. Remove blocking buffer.
8. Wash three times with PBS-T (10 mM phosphate buffer pH 7.4, 150 mM NaCl, 0.05% Tween 20).

Primary Antibody Reaction
1. Dilute (1:20) the monoclonal primary antibody (raised in chicken against SE) in PBS-T (10 mM phosphate buffer pH7.4, 150 mM NaCl, 0.05% Tween 20).
2. Add 200 μl of the diluted monoclonal antibody to each well.
3. Incubate at room temperature for 3 hours.
4. Remove antibody solution.
5. Wash three times with PBS-T (10 mM phosphate buffer pH 7.4, 150 mM NaCl, 0.05% Tween 20).

Application of Secondary Antibody
1. Dilute (1:2500) the enzyme-conjugated (HRP) secondary antibody in PBS-T(10 mM phosphate buffer pH 7.4, 150 mM NaCl, 0.05% Tween 20).
2. Add 200 μl of this solution to each well.
3. Incubate at room temperature for 2 hours.
4. Wash three times with PBS-T (10 mM phosphate buffer pH 7.4, 150 mM NaCl, 0.05% Tween 20).

Substrate Preparation
1. During the last incubation and immediately before use, prepare the enzyme substrate or bring the premade liquid substrate to room temperature.

Development
1. Add 200 μl of the freshly prepared substrate to each well.
2. Color should develop in positive wells after 30 minutes (orange for OPD).
3. Absorbence may be read directly in a microplate reader (450 nm for OPD) or the reaction may be stopped with 50 μl per well of the appropriate stopping reagent and absorbence read later (492 nm, for OPD).

Statistical Analysis

Statistical Analysis Software (SAS) was used for all the statistical differences found in these experiments.

Results

Figure 3:
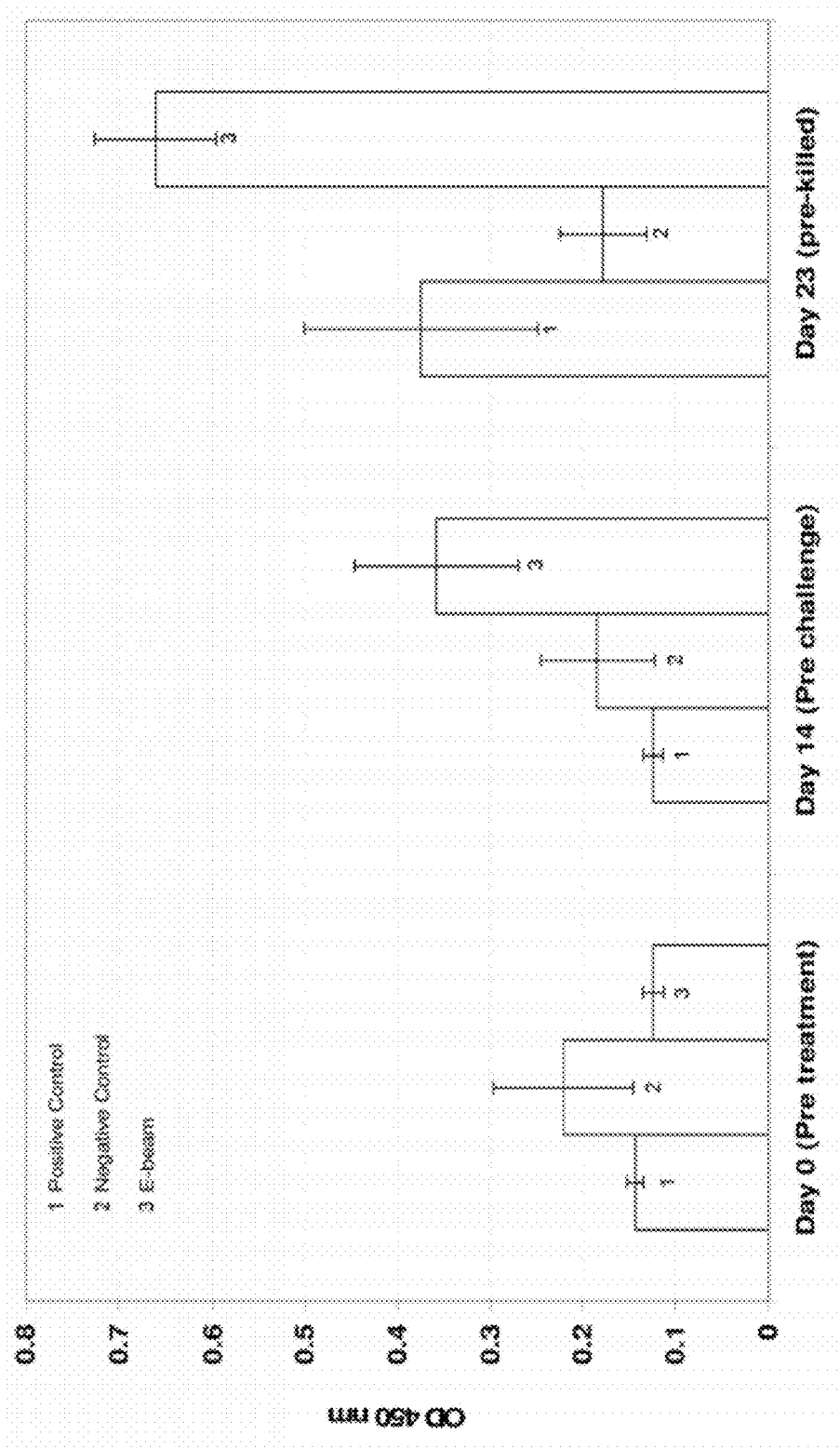
FIG. 3 shows the results from Example 1 of the antibody titration (ELISA) of laying hens challenged with *Salmonella enteritidis*.

The results are shown in FIGS. 1-3.

Example 2

A second trial was conducted to assess the effects of therapeutic administration (IM and in ovo) of the electron beam killed cell vaccine in protecting neonatal broiler chicks from *Salmonella typhimurium* (ST). Two experiments were conducted, to quantify the effects of the E beam vaccine (alone and with CPG) in layer chicks and to quantify the effects of the E beam vaccine (alone and with CPG) administered in ovo.

Experiment 1

In the first experiment of the present study, the effects of in ovo E-beamed ST or CPG administration were evaluated to measure heterophil function.

For this experiment, 400 Single comb White Leghorn (SCWL) embryos on day 18e (day 18 of incubation) were equally divided into four independent treatment groups, see below for treatment groups. Individual groups were placed in separate hatching trays and placed for hatch in the same hatching cabinet to provide identical hatching conditions. On day-of-hatch, the total number of chicks hatched in each treatment group were divided equally, half of the birds were used for heterophil function assays four days post hatch. For the collection of blood samples from chicks in each treatment group, all chicks were bled by decapitation and bled into EDTA tubes. Functional assays included: phagocytosis, degranulation, and oxidative burst activity were measured by the process below.

Experiment 2

In the second experiment of the present study, the effects of in ovo E-beamed ST or CPG administration were evaluated to measure heterophil function.

For this experiment, 400 broiler embryos on day 18e were equally divided into four independent treatment groups, see below for treatment groups. Individual groups were placed in separate hatching trays and placed for hatch in the same hatching cabinet to provide identical hatching conditions. On day-of-hatch, the total number of chicks hatched in each treatment group were divided equally, half of the birds were used for the in vivo ST challenge. These chicks received a booster vaccination at day 7 by IM injection (see concentrations below). Eleven days after the booster vaccination the chicks were challenged with $1\times10^6$ ST. Five days after challenge the birds were terminated and samples evaluated for ST.

Treatment Groups:

| Group | Feed | Treatment Groups | In Ovo | D7 Boost | N= |
|---|---|---|---|---|---|
| 1 | CSLS | Neg Control | Sham/Saline | − | 100 |
| 2 | CSLS | Positive Control | Sham/Saline | − | 50 |
| 3 | CSLS | CPG | + | − | 100 |
| 4 | CSLS | E-beam ST | + | − | 100 |
| 5 | CSLS | CPG + E-Beam ST | + | − | 100 |
| 6 | CSLS | CPG | + | + | 50 |
| 7 | CSLS | E-beam ST | + | + | 50 |
| 8 | CSLS | CPG + E-Beam ST | + | + | 50 |

Chicks

On day 18 of embryogenesis, eggs were obtained and treatment groups received the appropriate treatment and the negative and positive controls received a sham injection of saline. Upon hatch, chicks were divided into experimental groups and placed into individual floor rearing pens on clean pine shavings at age appropriate temperature and given feed and water ad libitum. Birds were fed a commercial corn soy layer starter diet from day 0.

In Ovo Injections:

In treatment groups where selected bacteria and adjuvants were administered in ovo, all injections occurred on day 18e to simulate commercial hatchery in ovo injection practices. Following in ovo injection, all viable embryos were transferred to hatching cabinets until hatch. All injections were performed according to previously published methods with slight modification. The large end of all eggs was wiped with 70% ethanol and gently scored with an 18-gauge needle. In the present investigation, either E-beamed. ST or CPG were administered into the amnion using a 1 cc tuberculin syringe and a 25-gauge needle equipped with a modified needle guard to limit all injections to a depth of 3 cm. Following in ovo injections to individual embryos, injection sites on all eggs were covered with melted paraffin using a cotton swab.

E-beamed ST for In Ovo and IM Injection

The following steps were followed to make the overnight culture:

1CFU was taken from storage plate. The culture was grown in 37° C. for 18-24 hours. The optical density (OD) of the culture was measured and recorded, and adjusted to an OD of 0.5 by serial dilutions. This gave an approximate concentration of $1 \times 10^7$ CFU/mL. This suspension was taken to the High Energy Electron-beam (E-beam) Irradiation facility at Texas A&M University.

This concentration of ($1 \times 10^7$ CFU/ml of ST cells (in log growth)) was irradiated at 2.5 kGy to inactivate/kill the cells. These cells were kept on ice until administered. This yielded a concentration of killed $1 \times 10^7$ CFU/ml of ST cells. The birds were administered $1 \times 10^4$ CPU/bird/treatment.

Cells were observed with a blacklight kit to determine if the cells were dead or alive. Cells that were alive would illuminate as green, and the dead or injured cells would illuminate as orange to red, depending on the severity of the damage to the cell.

CPG Preparation

Synthetic ODNs were purchased from BioSource International (Camarillo, Calif., USA) and further purified by ethanol precipitation. The sequences of the synthetic oligodeoxynucleotide (ODN) containing unmethylated CpG-dinucleotides (CpG-ODN) used in the present study were described by He et al. (2003, Identification of CpG oligodeoxynucleotide motifs that stimulate nitric oxide and cytokine production in avian macrophage and peripheral blood mononuclear cells. Dev. Comp. Immunol. 27, 621-627). The concentration of CpG ODN was 20 ug/bird or embryo.

Bacterial Strain for Challenge

A primary poultry isolate of *Salmonella typhimurium* (phage type 13A) from the NaTional Veterinary Services Laboratory, Ames, Iowa, was used. The challenge inoculum was prepared from an overnight culture which had been previously transferred three times in trypticase soy broth. The culture was serially diluted in sterile phosphate-buffered saline to a concentration of approximately $10^6$ cfu per mL. The cfu of the challenge inoculum was confirmed by plating onto DCA brilliant green agar (BGA) plates.

Recovery of *Salmonella*

All samples tested for *Salmonella* (+/−) including ceca, crop, liver, spleen and ovary were minced with sterile scissors and cultured. The organ samples were incubated for 24 h at 41° C. in Rappaport-vassiliadis R10 broth (Difco). After incubation, the broth was streaked onto a brilliant green agar (BGA) plate, incubated for an additional 24 h at 37° C., and examined for the presence of ST colonies. Samples that were direct plated for total cfu's were stomached and 0.25 g of cecal or crop contents were placed into a 6 mL snap cap polypropylene tube containing 2.25 mL of Butterfield's solution. Serial dilutions of each sample were performed using 0.5 mL of the sample, placed into 4.5 mL of Butterfield's solution for a final concentration of 10, 100, and 1000 cfu/mL. One hundred µL from each dilution tube was placed onto a BGA plate and spread plated using a bacterial cell spreader. All of the plates were incubated for 24 h at 37° C., and the number of *Salmonella* cfu were determined and expressed as $\log_{10}$ *Salmonella*/g cecal or crop contents. Cecal and crop contents that were negative at a 100 fold dilution on BGA plates but were positive at a 10 fold dilution on BGA plating were assigned 1.00 $\log_{10}$ *Salmonella*/g cecal contents. Suspect colonies were Confirmed by biochemical tests on triple sugar-iron agar and lysine-iton agar (Oxoid, Unipath Ltd., Hampshire, England) and further identified as ST serologically using *Salmonella* O antiserum group D, factors 1, 9, 12 (Difco).

Isolation of Heterophils

Collection of peripheral blood and heterophil isolation were conducted as previously described. Briefly, peripheral blood from approximately 50 chicks was pooled, mixed with 1% methylcellulose (1:1 v/v), and centrifuged at 25×g (rcf) for 15 min. The supernatant was removed, diluted with $Ca^{2+}$- and $Mg^{2+}$-free Hanks balanced salt solution, carefully layered onto a discontinuous Histopaque gradient (specific gravity 1.077/1.119) in 50-ml conical centrifuge tubes, and centrifuged at 250×g for 60 min. The heterophils, below the Histopaque 1.077/1.119 interface, were collected, washed, and re-suspended in RPMI-1640. Heterophils were counted and kept on ice until used.

Oxidative Burst Assay

Production of ROS by neonatal chicken heterophils during oxidative burst was measured by oxidation of DCFH-DA to fluorescent DCF as described by He et al (2003) with modification. One Milliliter of Chicken heterophils ($8 \times 10^6$ cells/ml) were pre-incubated in 2-ml microcentrifuge tubes for 1 hr at room temperature with or with out inhibitors; then, agonists and DCFH-DA (10 ug/ml in final concentration) were added to cells and continued incubation for 1 hr. The aliquots of cell cultures (150 µl) were then dispensed to black 96-well plates and the fluorescence was measured using a GENios Plus Fluorescence Microplate Reader (TECAN US Inc, Research Triangle Park, N.C.) at 485 nm excitation and 530 nm emission wavelengths (manually set the gain at 50). The fluorescent units (RFU) were recorded at 60-minute intervals for additional. 2 hr.

Degranulation-Assay

Solutions:
1. Buffer: [0.1M] Sodium Acetate
   FW=136.1, 136.1 gm/liter=[1M].
   1000 mls [0.1M] Sodium acetate.
   136.1/1000=0.1361(0.1) (1000)=13.61 gm in 1 liter of $dH_2O$ with 0.1% Triton X-100.
   Final pH=4.0.

2. Substrate: Prepared Fresh Daily (Chemical in −20 Freezer)
10 ml of substrate solution needed for 1, 96 well plate, formula below was for 10 ml.
[10 mM] 4-methylumbelliferyl-β-D-glucuronide (FW=352.3) in [0.1M] sodium acetate with 0.1% Triton X-100.
352.3/1000 (0.01) (10)=0.035 gm in 10 ml sodium acetate buffer used 50 μl/well in assay.
3. Standard Solution:
Stored 4C in dark several weeks.
[5 mM] 4-methylumbelliferone in ETOH (FW=198.2) Make in 50 ml batches.
198.2/1000(0.005)(50)=0.05 gm in 50 ml ETOH (95-100%). Prior to use diluted desired volume for assay 1:100
(20 ul in 1920 ul) in sodium acetate buffer (1:100 makes 50 uM).
Made desired standard dilutions in acetate buffer with 0.1% Triton X-100.
Dilutions needed for standard curve: [uM] 0.8, 1.56, 3.12, 6.25, 12.5, 25, 50=7 standards.
4. Stop Solution:
Made 1000 ml store at RT.
[0.05M] Glycine (FW=75.07).
[5 mM] EDTA (FW=372.2).
Final pH=10.4 (pH with [1M] NaOH).
Glycine
75.09/1000 (0.05) (1000)=3.8 gm.
EDTA (use ultra pure grade from Sigma sodium salt, not free acid).
372.2/1000 (0.005)(1000)=1.86 gm.
Added above 2 ingredients to 1000 ml $dH_2O$.
Final pH=10.4.
pH with [1M] NaOH.
Assay:

Chicken heterophils were isolated by previously described procedures. $8 \times 10^6$ heterophils were incubated with appropriate stimulants and/or inhibitors. The reaction was stopped by transferring tubes containing samples to an ice bath for 5-10 min., and then centrifuged at 250×g (2,000 rpm) for 10 min. at 4° C. Supernatants were removed from each sample stored at 4° C. and used for assay (supernatant samples may stored overnight for assay, but storage longer than 24 hours would yield inadequate results). 25 μl of each sample supernatant or the appropriate standard was added to each well (8 wells/sample) in a Costar flat bottom ELISA plate #3915, non-treated, opaque (black) and incubated with 50 μl of freshly prepared substrate at 41° C. for 4 h. The Black ELISA plate was covered with another black plate turned up-side down to ensure minimal light exposure to the samples/standards. The Reaction was stopped by adding 200 μl of Stop Solution. Liberated 4-methylumbelliferone was measured fluorimetrically (excitation: 355 nm, emission: 460 nm) with a fmax (molecular devices, software softmax) fluorimeter. Values were determined by extrapolating from a standard curve.

Heterophil Phagocytosis Assay

The heterophil phagocytosis assay used Heterophils [$5 \times 10^6$ cells/ml], Salmonella enteritidis [$5 \times 10^7$ cfu] (working ratio 10 SE: 1 Heterophil) as below:

Combined Heterophils 1 ml+SE 1 ml in a 15 ml sterile conical centrifuge tube, centrifuged for contact 2,000×g 15 minutes 4° C.

Incubated at 39° C.+5% $CO_2$ for 1 hour.
Submerged in ice bath 15 minutes.
Washed with ice cold clear RPMI, 2,000×g 15 minute 4° C.
Resuspended pellet in ice cold Gentamicin [100 μg/ml], diluted in clear RPMI and incubate 1 hour on rocker at 37° C. (this temperature was critical, as Gentamicin is not stable at temperatures above 37° C.).
Washed 3× in ice cold clear RPMI, 2,000×g 15 minutes, each wash.
Made 3-5 cytospins of each treatment group for microscopic counts.

Statistical Analysis

Chi-square analysis was used to determine significant differences between treatment groups for incidences of SE colonization of the crop, ceca, liver, spleen and ovary (Luginbuke and Schlotzhauer, 19837). Differences in the $Log_{10}$ cfu of SE counts and functional assays among treatment groups were determined by analysis of variance using the general linear models procedures. Significant differences were further separated using Duncan's multiple range tests and commercial statistical analysis software (SAS Institute, Cary, N.C.). All data analyzed by statistical analyses were considered significant at ($P \leq 0.05$).

Results

Figure 4:
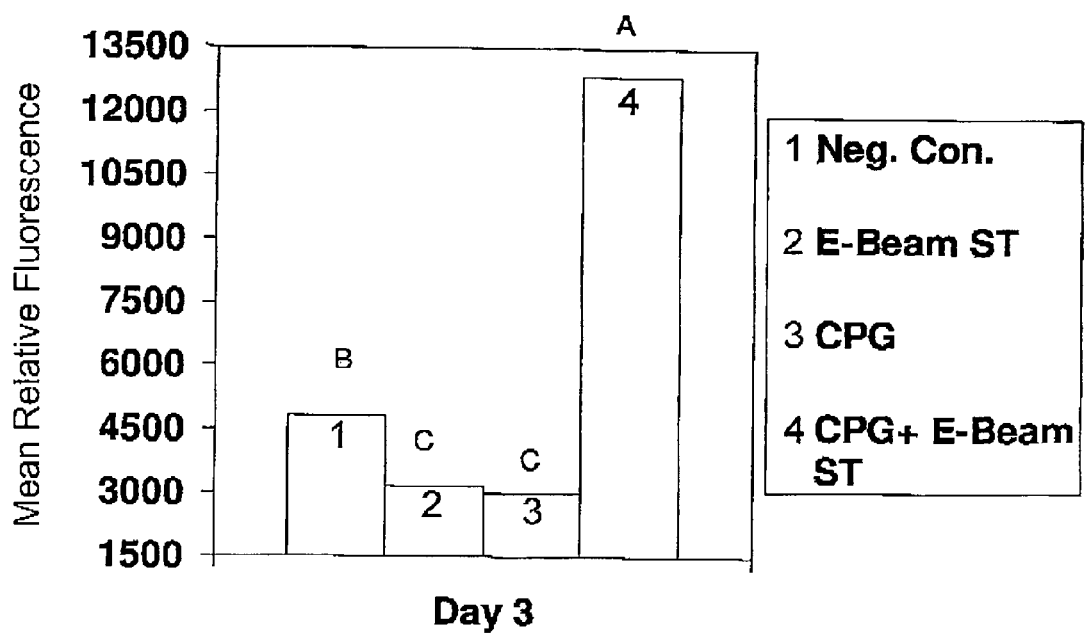
FIG. 4 shows the results from Example 2 of the heterophil oxidative burst in broiler chicks.
Figure 5:
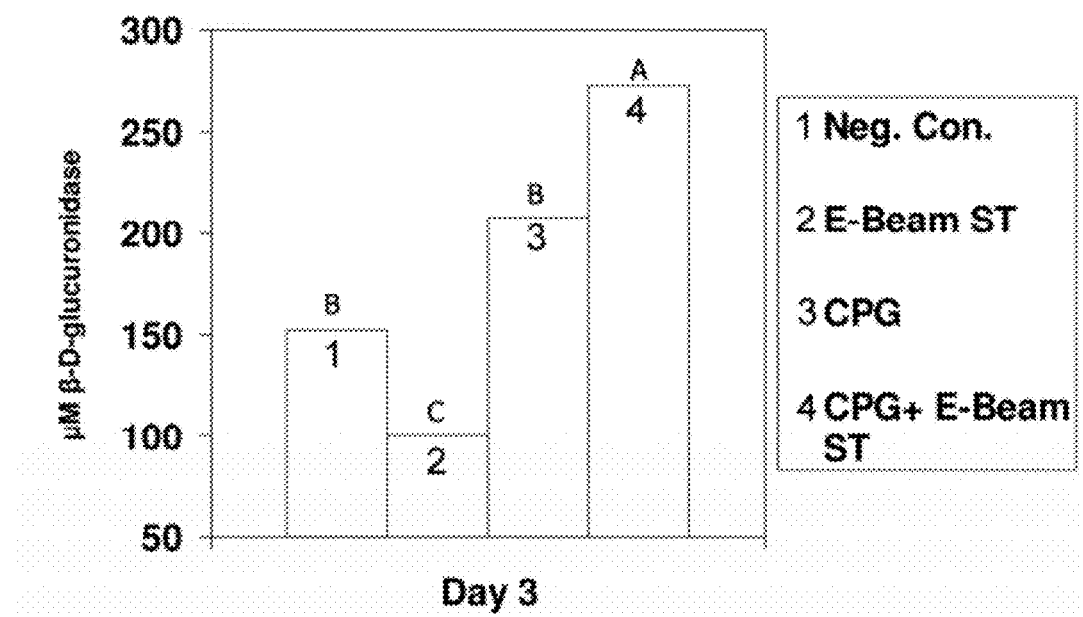
FIG. 5 shows the results from Example 2 of the heterophil degranulation in broiler chicks.
Figure 6:
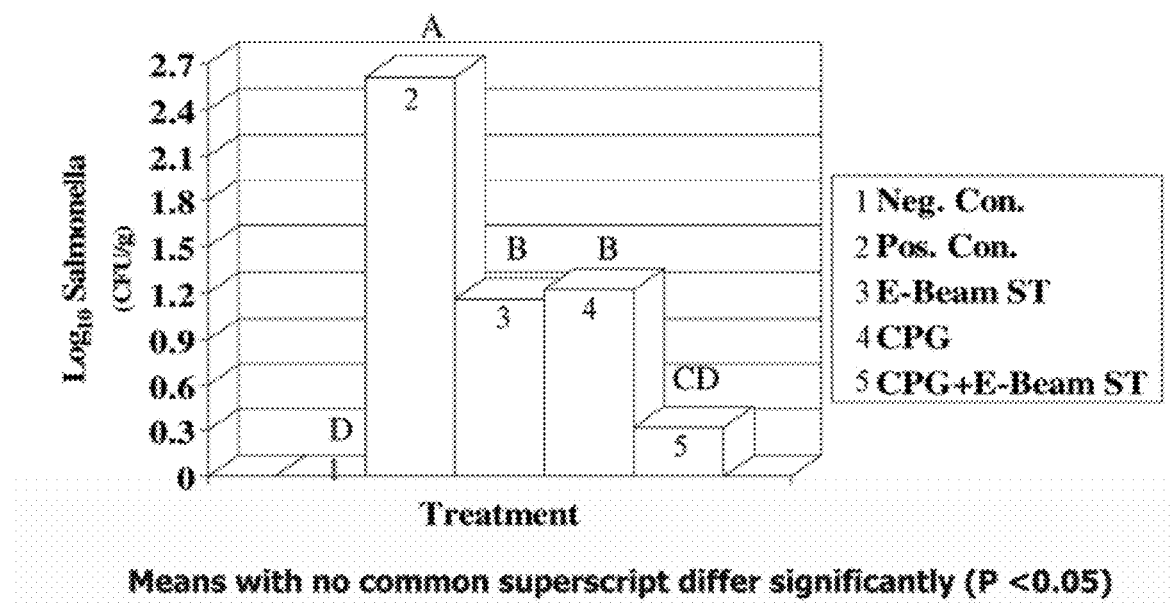
FIG. 6 shows the results from Example 2 of the colonization by *Salmonella typhimurium* in the ceca of broiler chicks.

The results are shown in FIGS. 4-6. Means with no common superscript differ significantly.

It is understood that the foregoing detailed description is given merely by way of illustration and that modifications and variations may be made therein without departing from the spirit and scope of the invention.

We claim:

1. A composition comprising an immunologically effective amount of electron beam killed cells of Salmonella species in a pharmaceutically acceptable carrier, wherein said killed cells are produced by exposing whole, intact cells of a Salmonella species to irradiation with a high energy electron beam under conditions effective to kill said cells while retaining the ability to elicit a protective immune response in an animal against said Salmonella species.

2. The composition of claim 1 wherein said Salmonella is selected from the group consisting of Salmonella typhimurium and Salmonella enteritidis.

3. The composition of claim 1 further comprising an adjuvant.

4. The composition of claim 3 wherein said adjuvant is selected from the group consisting of Freund's incomplete adjuvant, Freund's complete adjuvant, alum, microparticles, nanoparticles, beads, and oil.

5. The composition of claim 1 wherein said exposing comprises irradiating said cells with said high energy electron beam at a dose between approximately 2 kGy and approximately 5 kGy.

6. The composition of claim 5 wherein said exposing comprises irradiating said cells with said high energy electron beam at a dose of between approximately 2.5 kGy and approximately 4.0 kGy.

7. A method for controlling a Salmonella species in an animal comprising administering to said animal a composition comprising an immunologically effective amount of killed cells of said Salmonella species in a pharmaceutically acceptable carrier, wherein said killed cells are produced by exposing whole, intact cells of said Salmonella species to irradiation with a high energy electron beam under conditions effective to kill said cells while retaining the ability to elicit a protective immune response in an animal against said *Salmonella* species.

8. The method of claim 7 wherein said animal is selected from the group consisting of fowl, ovine, bovine, and porcine.

9. The method of claim 7 wherein said animal comprises poultry selected from the group consisting of chickens, turkeys, ducks, quail, and geese.

10. The method of claim 7 wherein said *Salmonella* species is selected from the group consisting of *Salmonella typhimurium* and *Salmonella enteritidis*.

11. The method of claim 9 wherein said composition is administered in ovo.

* * * * *